United States Patent [19]

Jones et al.

[11] 4,111,906

[45] Sep. 5, 1978

[54] POLYIMIDES PREPARED FROM PERFLUOROISOPROPYLIDENE DIAMINE

[75] Inventors: Robert J. Jones, Hermosa Beach; Michael K. O'Rell, Manhattan Beach; Jim M. Hom, Sepulveda, all of Calif.

[73] Assignee: TRW Inc., Redondo Beach, Calif.

[21] Appl. No.: 706,880

[22] Filed: Jul. 19, 1976

[51] Int. Cl.$^2$ .............................................. C08G 73/10
[52] U.S. Cl. .................................... 528/229; 260/571; 528/337; 528/341; 528/344; 528/345; 528/346; 528/348; 528/332; 528/350; 528/353
[58] Field of Search ............................ 260/47 CP, 571

[56] References Cited

U.S. PATENT DOCUMENTS 3,649,601  3/1972  Critchley et al. ............... 260/78 TF
3,925,312  12/1975  Fletcher et al. .................. 260/47 CP
3,944,575  3/1976  Villaescusa et al. .................. 260/395

Primary Examiner—Lester L. Lee
Attorney, Agent, or Firm—Donald R. Nyhagen; Alan D. Akers

[57] ABSTRACT

This invention relates to a novel aromatic diamine and more particularly to the use of said diamine for the preparation of thermally stable high-molecular weight polymers including, for example, polyamides, polyamideimides, polyimides, and the like. This diamine is obtained by reacting a stoichometric amount of a disodium salt of 2,2-bis(4-hydroxyphenyl) hexafluoropropane with 4-chloronitrobenzene to obtain an intermediate, 2,2-bis[4-(4-nitrophenoxy)phenyl] hexafluoropropane, which is reduced to the corresponding 2,2-bis[4-(4-aminophenoxy)phenyl] hexafluoropropane.

3 Claims, No Drawings

POLYIMIDES PREPARED FROM PERFLUOROISOPROPYLIDENE DIAMINE

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

Polyimides, because of their outstanding thermal stability, have been favored for use in advanced engineering structures. In the past, polyimides were difficult to fabricate because of their insolubility in most of the more common solvents. The solubility problem was partially solved by using a polyamide-acid intermediate for product fabrication. During the final fabrication steps, imidization of the polyamide-acid is easily accomplished to give the desired end product. While this solved the solubility problem, it did not successfully solve a void problem caused by water liberated during imidization when the polyamide-acid was cured. The presence of voids in the final product is very undesirable because they reduce the mechanical properties of the product.

In U.S. Pat. No. 3,528,950, a solution to the void problem was offered. In this patent, a fully imidized prepolymer having reactive end groups was formed. In this way, the water of imidization was removed before final cure of the prepolymer during fabrication of the polyimide product. Although this substantially solved the void problem, solvent solubility was not as desirable as many fabricators would prefer.

Subsequently, U.S. Pat. No. 3,812,159 taught that a dianhydride monomer containing a phenoxyphenyl sulfone linkage could be used in the process taught by U.S. Pat. No. 3,528,950, and which would provide polyimides with improved solubility. The characteristics and synthesis methods for these polyimides are taught in U.S. Pat. No. 3,699,075.

SUMMARY OF THE INVENTION

While U.S. Pat. No. 3,812,159 solves the solubility problem, the high temperature stability of the sulfone containing polyimide is not as desirable as it could be. Thus, the present invention seeks to improve the chemical and thermal stability of polyimides by incorporating an aromatic fluorine diamine compound into the polymeric chain while maintaining their solubility characteristics as discussed in the background. The compound may be characterized by the following formula:

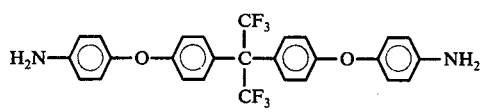

This compound is synthesized by an aromatic nucleophilic substitution of the chloro group on 4-chloronitrobenzene with a phenoxide ion. This reaction is taught in substantial detail in Ser. No. 113,747, filed Feb. 8, 1971. The resultant dinitro coupling compound is then reduced to the desired diamine. Polyimides having hexafluoro substitutents in the polymer structure can be synthesized by reacting the diamine with an appropriate dianhydride.

DESCRIPTION OF THE PREFERRED EMBODIMENTS

Preparation of a high molecular weight diamine having the formula:

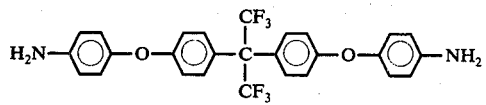

is initiated by reacting stoichiometric amounts of 2,2-bis(4-hydroxyphenyl) hexafluoropropane with sodium hydroxide to produce the disodium salt according to the following:

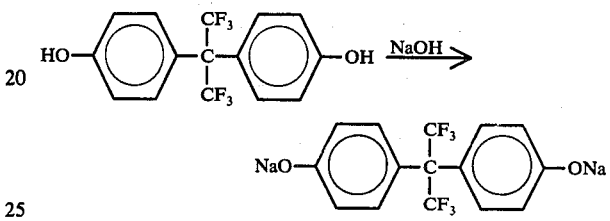

This reaction produces an intermediate compound which is sufficiently active to enter into a nucleophilic displacement reaction with the chloro-substituent on 4-chloronitrobenzene to produce 2,2,-bis[4-(4-nitrophenoxy)phenyl] hexafluoropropane according to the following:

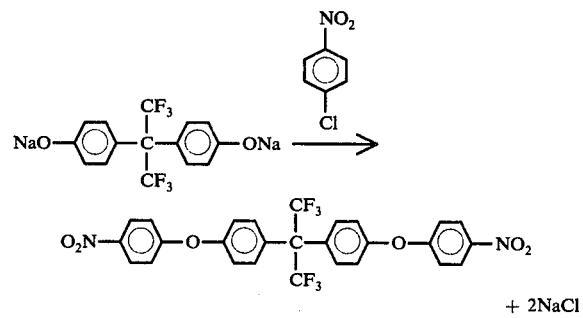

+ 2NaCl

Reduction of the dinitro compound to the corresponding diamine is accomplished by reacting the compound in the presence of activated iron and water, stannous chloride, or hydrogen with a palladium catalyst.

The following examples teaches the preferred method of synthesizing 2,2-bis[4-(4-aminophenoxy)phenyl] hexafluoropropane.

EXAMPLE I

Approximately 26.9 gm. (0.08 mole) of 2,2-bis(4-hydroxyphenyl) hexafluoropropane was dissolved in 120 gm of dimethyl acetamide and 60 ml toluene containing 6.8 gm (0.17 mole) sodium hydroxide and 3 ml water. The mixture heated to reflux and the wate was removed by means of a Dean-Stark trap. After all of the water was removed, the toluene was removed by distillation until the pot temperature reached 150° C.

To the disodium salt prepared above in 150 g dimethyl acetamide was added 31.51 g (0.2 mole) 4-chloronitrobenzene. The reaction mixture was heated at 150° C for 48-hours and then poured into 1000 ml water. The yellow precipitate was collected by filtration and washed well with water. Recrystallization from ethanol afforded 43 g (93%) of 2,2-bis[4-(4-nitrophenoxy)phenyl] hexafluoropropane; mp 158°–160° C. A mixture of 11.56 g (0.02 mole) 2,2-bis[4-(4-nitrophenoxy)phenyl] hexafluoropropane, 8.96 g (0.16 mole) powdered iron and 20 ml of ethanol were added to a 100 ml three-necked flask. The mixture was heated to reflux and then a solution of 0.14 ml (6 mmole) of hydrochloric acid in 5 ml of ethanol was added dropwise with vigorous stirring. The mixture was refluxed for 2-hours, then made alkaline to litmus by adding alcoholic potassium hydroxide. The mixture was filtered hot and the filter cake was boiled twice with fresh ethanol to remove all of the amine. The filtrate was cooled and 300 ml of concentrated hydrochloric acid was added. The resulting amine hydrochloride was collected by filtration and washed with ethanol. The dihydrochloride then was dissolved in water (150 ml) and 5 percent (w/v) sodium hydroxide was added until the mixture was alkaline to litmus. The insoluble diamine was collected by filtration and then recrystallized from ethanol to give 6.3 g of nearly colorless needles; mp 150°–152° C.

ANALYSIS: Calculated for $C_{27}H_{20}N_2O_2F_6$: C, 62.43; H, 3.94; N, 5.27. Found: C, 62.55; H, 3.88; N, 5.40.

As suggested previously, this diamine can be used to produce polyimides or polyamides when reacted with a diacid, a dianhydride, or a diacid halide. Because of the fluorine substituent on the diamine, the resulting polyimides or polyamides have improved chemical and thermal stability. The reaction of 2,2-bis[4-(4-aminophenoxy)phenyl] hexafluoropropane with a dianhydride will produce a polyimide which can be illustrated by the idealized formula:

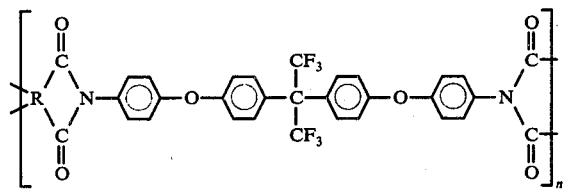

wherein n is an integer sufficient to provide a structure having an average molecular weight of at least 5000 and R is an organic radical of 5 to 22 atoms which may be an aliphatic radical, including alicyclic, or an aromatic radical having one or more benzene rings or fused polynuclear rings. These polyimides can be used as a matrix for laminated glass or graphite structures having high thermal stability, for example, ablative structures. High temperature coatings and adhesives are a few additional applications for which these polyimides are particularly suited.

In an analogous reaction, 2,2-bis[4-(4-aminophenoxy)phenyl] hexafluoropropane can be reacted with a diacid to produce a polyamide having improved thermal stability and flexibility characteristics compared to the prior art polyamides.

Examples of a few of the dianhydrides which are suitable for preparation of polyimides are:

TABLE I pyromellitic dianhydride benzophenone tetracarboxylic dianhydride
2,3,6,7-naphthalene tetracarboxylic dianhydride
3,3',4,4'-diphenyl tetracarboxylic dianhydride
1,3,5,6-naphthalene tetracarboxylic dianhydride
2,2',3,3'-diphenyl tetracarboxylic dianhydride
2,2-bis(3,4-dicarboxyphenyl)propane dianhydride
3,4,9,10-perpylene tetracarboxylic dianhydride
bis(3,4-dicarboxyphenyl)ether dianhydride
ethylene tetracarboxylic dianhydride
naphthalene-1,2,4,5-tetracarboxylic dianhydride
naphthalene-1,4,5,8-tetracarboxylic dianhydride
decahydronaphthalene-1,4,5,8-tetracarboxylic dianhydride
4,8-dimethyl-1,2,3,5,6,7-hexahydronaphthalene-1,2,5,6-tetracarboxylic diahydride
2,6-dichloronaphthalene-1,4,5,8-tetracarboxylic dianhydride
2,7-dichloronaphthalene-1,4,5,8-tetracarboxylic dianhydride
2,3,6,7-tetrachloronaphthalene-1,4,5,8-tetracarboxylic dianhydride
phenanthrene-1,8,9,10-tetracarboxylic dianhydride
cyclopentane-1,2,3,4-tetracarboxylic dianhydride
pyrrolidine-2,3,4,5-tetracarboxylic dianhydride
pyrazine-2,3,5,6-tetracarboxylic dianhydride
2,2-bis(2,3-dicarboxyphenyl)propane dianhydride
1,1-bis(2,3-dicarboxyphenyl)ethane dianhydride
1,1-bis(3,4-dicarboxyphenyl)ethane dianhydride
bis(2,3-dicarboxyphenyl)methane dianhydride
bis(3,4-dicarboxyphenyl)methane dianhydride
bis(3,4-dicarboxyphenyl)sulfone dianhydride
benzene-1,2,3,4-tetracarboxylic dianhydride
1,2,3,4-butane tetracarboxylic dianhydride
thiophene-2,3,4,5-tetracarboxylic dianhydride, etc.

Examples of a few of the suitable diacids are:

TABLE II 1,4-cyclohexanedicarboxylic acid
3,4'-benzophenone dicarboxylic acid
ethylene dicarboxylic acid
phthalic acid
maleic acid
adipic acid
succinic acid
malonic acid In addition to the compounds set forth in Tables I and II, supra, corresponding acid halides would be equally suitable reactants.

The following examples illustrate the method employed in preparing the polyimides in accordance with the invention:

EXAMPLE II

To a stirred solution of 1.04 g (2 mmole) of 2,2-bis[4-(4-aminophenoxy)phenyl] hexafluoropropane in 4.0 g of dimethylacetamide was slowly added portionwise 0.645 g (2 mmole) of benzophenone tetracarboxylic acid dianhydride (BTDA) at such a rate that each portion of dianhydride was allowed to dissolve before the next portion was added. The reaction was run under a nitrogen blanket and was cooled with a wate bath. The residual BTDA was washed into the reaction flasks with an additional 3 ml of dimethylacetamide to give a 19 percent by weight solids solution. The reaction mixture was stirred for three hours after the last of the BTDA had been added and then was transferred to a vacuum oven. The solvent was removed at 100° C. and the resulting amide/acid polymer was imidized by heating it to 180° C. for 4 hours. The tough flexible polymer was found to have an inherent viscosity of 0.47 dl/g ($H_2SO_4$ at 30° C.). Initial weight loss occurred at 420° C. in a TGA scan in air.

EXAMPLE III

Using the same procedure as described in Example II, a polyimide was prepared from 2,2-bis[4-(4-aminophenoxy)phenyl] hexafluoropropane (0.933 g, 1.8 mmole) and 2,2-bis[4-(3,4-dicarboxyphenoxy)phenyl] hexafluoropropane dianhydride (1.130 g, 1.8 mmole). The amide/acid polymer was imidized by heating it at 160° C. for 6 hours. The very tough film was found to have an inherent viscosity of 0.44 dl/g ($H_2SO_4$ at 30° C.).

It is obvious that anti-oxidants and/or stabilizers and the like may be used in combination with the polymeric materials if desired. Moreover, the polymeric materials obtained from the amines of this invention may be used in combination with various fillers and reinforcing agents including silica, glass, carbon black, metal, fibers, dye-stuffs, pigments, graphite, and various mixtures thereof.

We claim:

1. A polyimide consisting essentially of recurring units:

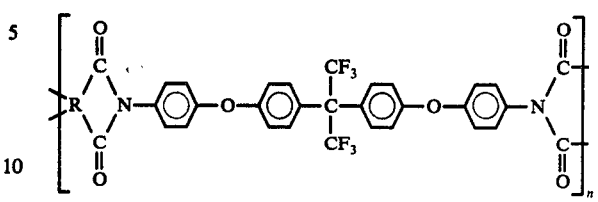

where $n$ is an integer sufficient to provide a structure having an average molecular weight of at least 5000 wherein R is an organic radical of 5 to 22 atoms selected from the group consisting of tetravalent aliphatic radicals and tetravalent aromatic radicals.

2. The polyimide according to claim 1 further characterized in that R has at least one benzene ring.

3. The polyimide according to claim 1 further characterized in that R has an arylene radical containing two benzene rings.

* * * * *

UNITED STATES PATENT AND TRADEMARK OFFICE
CERTIFICATE OF CORRECTION

PATENT NO. : 4,111,906
DATED : September 5, 1978
INVENTOR(S) : Robert J. Jones, et al.

It is certified that error appears in the above-identified patent and that said Letters Patent are hereby corrected as shown below:

Column 2, line 60 after "mixture" insert --was-- delete "wate" and insert --water-- therefor;

Column 4, line 3 delete "perpylene" and insert --perylene-- therefor;

line 57 delete "wate" and insert --water-- therefor.

Signed and Sealed this

Thirtieth Day of October 1979

[SEAL]

Attest:

RUTH C. MASON
Attesting Officer

LUTRELLE F. PARKER
Acting Commissioner of Patents and Trademarks